(12) United States Patent
Yang (10) Patent No.: US 10,478,606 B2
(45) Date of Patent: Nov. 19, 2019

(54) MEDICAL CONNECTOR

(71) Applicant: Sunder Biomedical Tech. Co., Taichung (TW)

(72) Inventor: Chao-Chin Yang, Kaohsiung (TW)

(73) Assignee: Sunder Biomedical Tech. Co., Taichung (TW)

(*) Notice: Subject to any disclaimer, the term of this patent is extended or adjusted under 35 U.S.C. 154(b) by 304 days.

(21) Appl. No.: 15/417,843

(22) Filed: Jan. 27, 2017

(65) Prior Publication Data

US 2018/0140819 A1 May 24, 2018

(30) Foreign Application Priority Data

Nov. 21, 2016 (TW) .............................. 105138056 A (51) Int. Cl.
*A61M 39/10* (2006.01)
*A61M 39/24* (2006.01)

(52) U.S. Cl.
CPC ............ *A61M 39/10* (2013.01); *A61M 39/24* (2013.01)

(58) Field of Classification Search
CPC ............ A61M 2039/268; A61M 39/26; A61M 39/10; A61M 2039/1072
See application file for complete search history.

(56) References Cited

U.S. PATENT DOCUMENTS 10,046,154 B2 * 8/2018 Fangrow ............... A61M 39/10

FOREIGN PATENT DOCUMENTS

TW            I537020         6/2016

* cited by examiner

*Primary Examiner* — Deanna K Hall
(74) *Attorney, Agent, or Firm* — Muncy, Geissler, Olds & Lowe, P.C.

(57) ABSTRACT

A conventional medical connector allows a gap therein to function as a passage for a flowing liquid at the cost of the flow rate of the flowing liquid. The present invention provides a medical connector which comprises a tubular resilient element. One end of the resilient element is a closed end. A through hole is disposed on the wall of the resilient element, allowing an infusion liquid to flow fluently through the cavity of the tubular resilient element. Therefore, the medical connector is effective in increasing the flow rate and thereby suitable for massive liquid infusion.

6 Claims, 8 Drawing Sheets

MEDICAL CONNECTOR

BACKGROUND OF THE INVENTION

1. Field of the Invention

The present invention relates to medical equipment and, more particularly, to a medical connector.

2. Description of the Prior Art

Medical treatment usually entails feeding liquids into the human body (for example, drips, and intravenous infusion medication) of a patient and draining liquids from the human body (for example, drawing blood) of the patient with various infusion pipelines. To facilitate operation, a cannula has one end connected to a vein of the patient and the other end equipped with a safety infusion female connector. When pushed by a dispensing end of a conventional syringe, the safety infusion female connector is opened and thus operable for use in intravenous infusion medication and drawing blood, thereby dispensing with the need to insert a needle into the patient's skin. Hence, the conventional infusion connector is safe to use and popular with medical professionals.

However, leakage of contents of the conventional syringe to the outside will pose a danger to medical professionals and patients, if the contents of the conventional syringe are a radioactive medication, an infectious body fluid, or a target tumor suppressor harmful to the human skin. Accordingly, it is necessary to develop a medical connector capable of leakage prevention.

Referring to Taiwan patent I537020, a conventional medical connector has a catheter and a moving element. The catheter has therein a guide rod. A gap is present between the catheter and the guide rod. The moving element in motion clears the gap and thus makes it ready to carry out infusion.

However, not only is the gap between the catheter and the guide rod used exclusively as a passage, but the gap is also of considerable length; as a result, the flow rate is too low to allow massive infusion to be time-efficient.

In view of its aforesaid drawback, the conventional medical connector still has room for improvement.

SUMMARY OF THE INVENTION

It is an objective of the present invention to provide a medical connector for use in massive liquid infusion.

In order to achieve the above and other objectives, the present invention provides a medical connector which comprises a receiving element, a moving element, and a resilient element. The receiving element has an enclosing wall, a first tube, and a second tube. A portion of the enclosing wall extends radially and inward to form a first end wall to connect with the first tube. The enclosing wall has an end extending radially and inward to form a second end wall to connect with the second tube. The first tube has one end which protrudes from the first end wall and has a mouth. The inner diameter of the first tube is the least at the mouth, and the first end wall has at least one first limiting aperture. The moving element has a basal portion and at least one protruding portion connected to the basal portion. The basal portion is disposed in the receiving element and has a second limiting aperture. The protruding portion penetrates the first limiting aperture and protrudes from the receiving element. The resilient element has a first peripheral wall extending in a circle to take on a tubular shape and a second peripheral wall extending in a circle to take on a tubular shape. The first peripheral wall has at least one through hole. The first peripheral wall has one end being a closed end. The first peripheral wall has the other end extending radially and outward to form a connection portion to connect with the second peripheral wall. The second peripheral wall has a free end abutting against the second end wall. The first peripheral wall and the second peripheral wall together define annularly a cavity in communication with the second tube. The first peripheral wall penetrates the second limiting aperture and is disposed in the first tube. The closed end movably closes the mouth. The connection portion abuts against the basal portion. The moving element moves from the first end wall to the second end wall and thereby presses against the second peripheral wall, causing the closed end to exit the mouth so that the resilient element is in an open state during which the mouth, the through hole, the cavity, and the second tube are in communication with each other.

Regarding the medical connector according to a preferred embodiment of the present invention, the inner diameter of the first tube increases gradually from the mouth to the first end wall, and the outer diameter of the first peripheral wall increases gradually with the inner diameter of the first tube.

Regarding the medical connector according to a preferred embodiment of the present invention, the first tube closes the through hole as soon as the closed end closes the mouth.

Regarding the medical connector according to a preferred embodiment of the present invention, the inner diameter of the second peripheral wall is larger than the inner diameter of the first peripheral wall.

Regarding the medical connector according to a preferred embodiment of the present invention, the vertical distance between the protruding portion and the first end wall is less than the vertical distance between a free end of the first tube and the first end wall.

Regarding the medical connector according to a preferred embodiment of the present invention, the basal portion further has a first flange protruding toward the second end wall and fitting around the second peripheral wall.

Regarding the medical connector according to a preferred embodiment of the present invention, the second end wall further has two second flanges protruding toward the first end wall, and the free end of the second peripheral wall is clamped between the two second flanges.

Regarding the medical connector according to a preferred embodiment of the present invention, a third flange is disposed on an outer wall surface of the first peripheral wall and disposed between the through hole and the connection portion to abut against an inner wall surface of the first tube in the open state.

Regarding the medical connector according to a preferred embodiment of the present invention, a fourth flange is disposed on an inner wall surface of the first tube so that the fourth flange is abuttingly disposed between the through hole and the connection portion in the open state.

The medical connector of the present invention not only uses the closed end to prevent a liquid from leaking out of the mouth, but also uses the cavity annularly defined by the first peripheral wall and the second peripheral wall as a passage for infusion. Hence, the medical connector of the present invention is conducive to enhancement of flow rate and thus applicable to massive liquid infusion.

Features of the present invention are described in detail later. However, persons skilled in the art understand that the detailed description and specific embodiments of the present invention are illustrative of the present invention rather than restrictive of the claims of the present invention.

DETAILED DESCRIPTION OF THE EMBODIMENT OF THE INVENTION

Referring to FIGS. 1~5, a medical connector 10 of the present invention comprises a receiving element 20, a moving element 30, and a resilient element 40.

Figure 1:
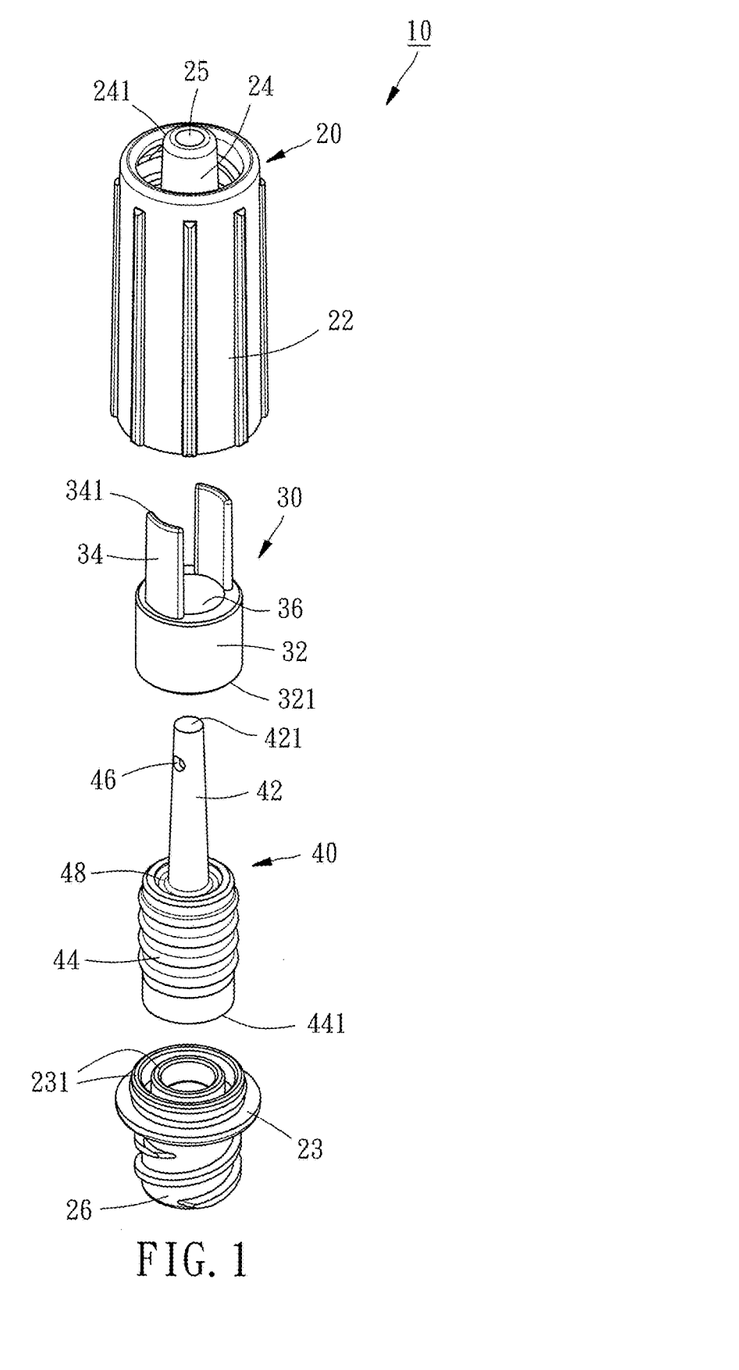
FIG. 1 is an exploded view of a medical connector of the present invention.
Figure 2:
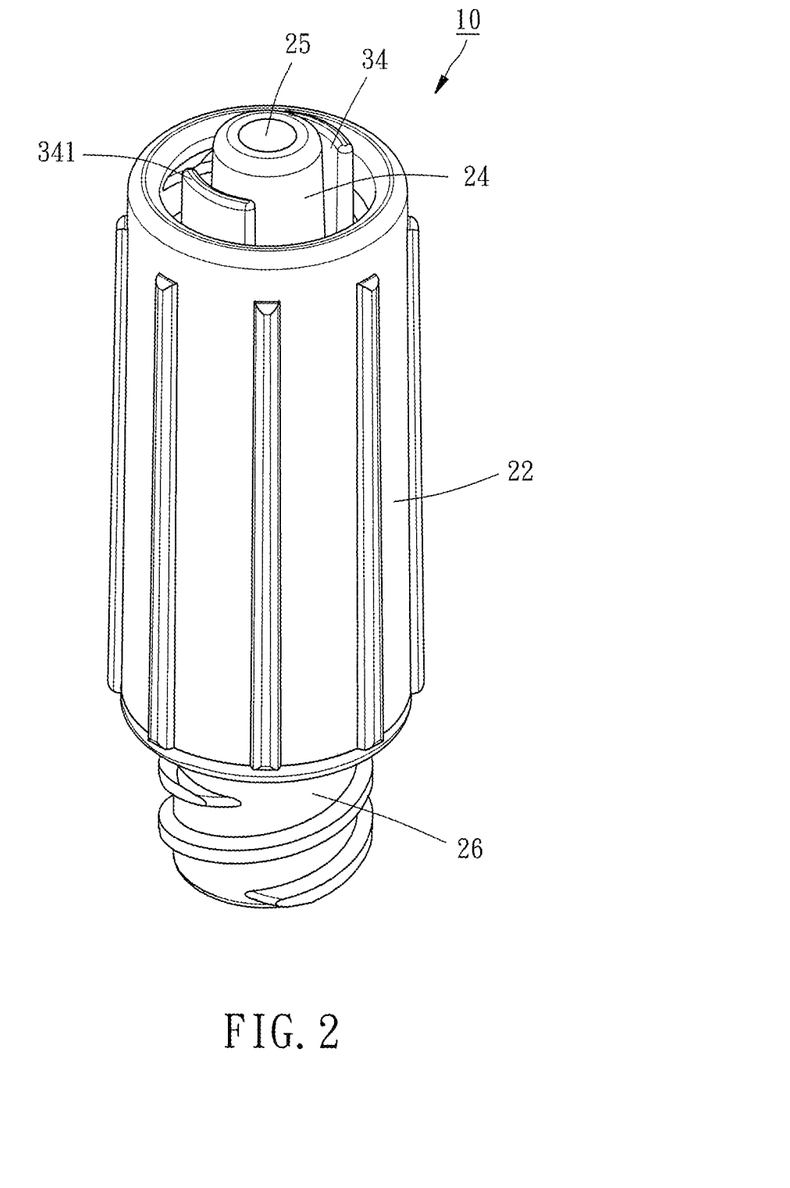
FIG. 2 is a perspective view of the medical connector of the present invention.
Figure 3:
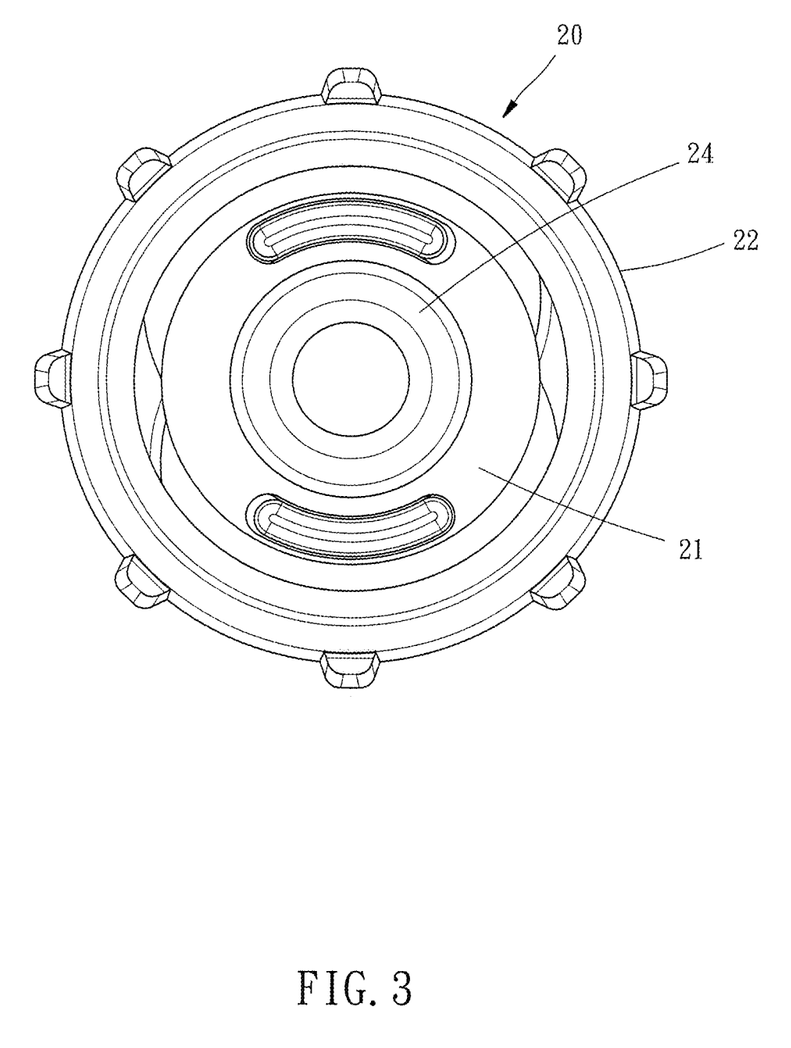
FIG. 3 is a top view of the medical connector of the present invention.
Figure 5:
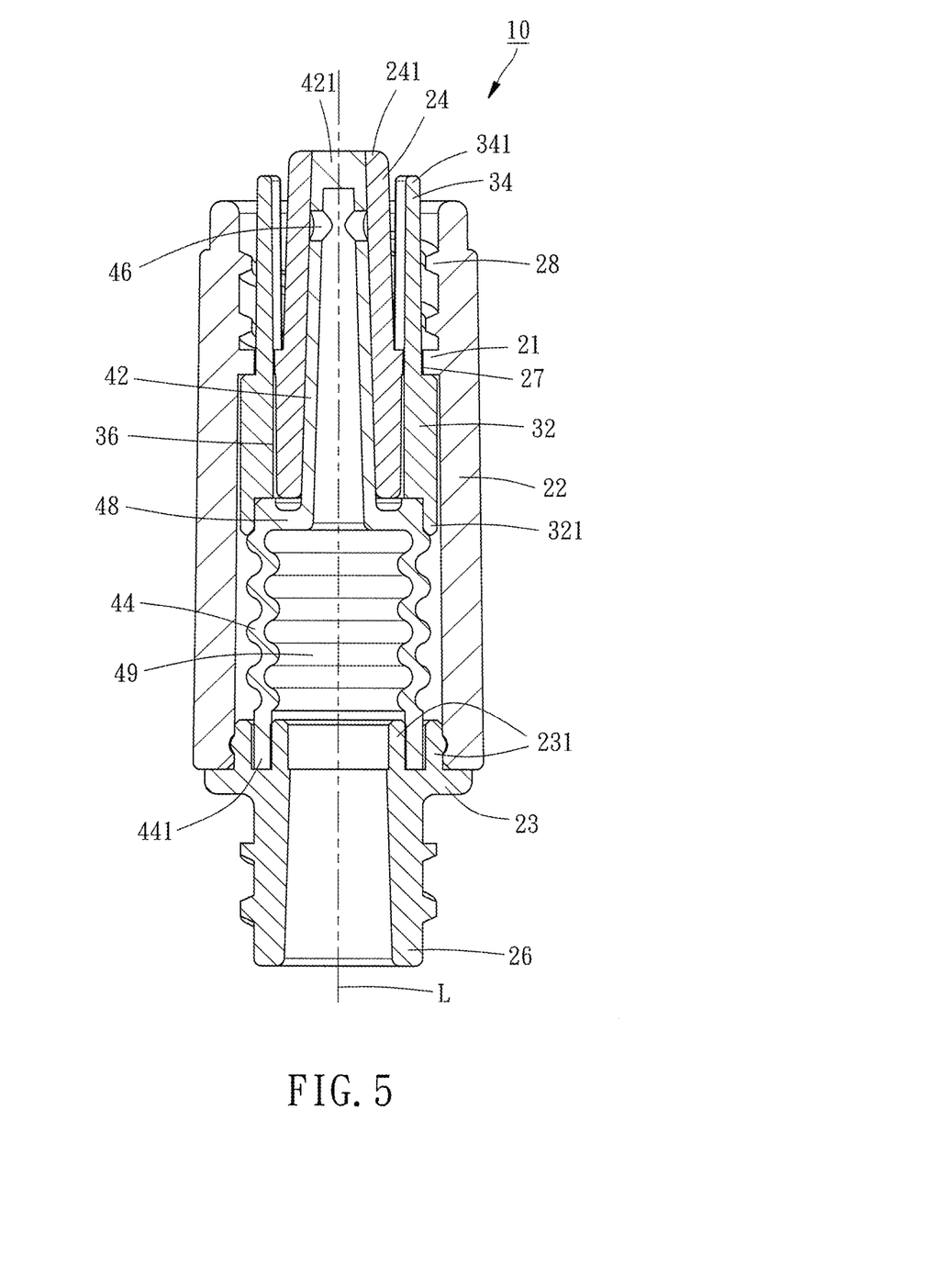
FIG. 5 is a cross-sectional view of the medical connector taken along line 5-5 of FIG. 4.
Figure 6:
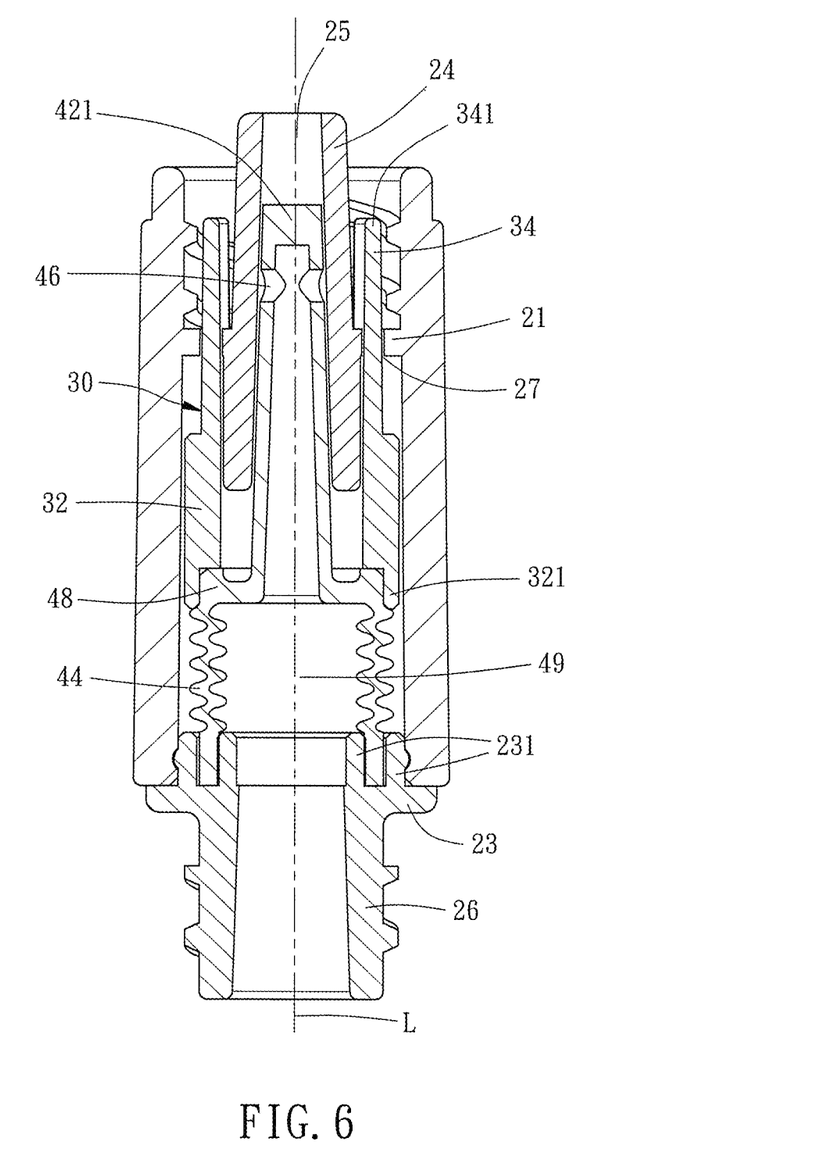
FIG. 6 is a schematic view of circulation in the medical connector with reference to FIG. 5.

The receiving element 20 has an enclosing wall 22, a first tube 24, and a second tube 26. Referring to FIGS. 1, 5, a portion of the enclosing wall 22 extends radially and inward to form a first end wall 21 to connect with the first tube 24. One end of the enclosing wall 22 extends radially and inward to form a second end wall 23 to connect with the second tube 26, whereas the other end of the enclosing wall 22 is not connected to any other component and thus is known as a free end. Referring to FIGS. 3, 6, the first tube 24 has a free end 241 which protrudes from the first end wall 21. The free end 241 has a mouth 25. The inner diameter of the first tube 24 is the least at the mouth 25. The first end wall 21 has two first limiting apertures 27. The second end wall 23 and the enclosing wall 22 are shown separate in FIG. 1 to highlight the spatial relationships of components. The free end 241 of the first tube 24 functions as a male connector compatible with luer specifications.

For illustrative sake, the center of the first tube 24 and the center of the second tube 26 are connected by an imaginary connection line L to thereby define a direction parallel to the imaginary connection line L as an axial direction and define a direction perpendicular to the axial direction as a radial direction.

The moving element 30 has a basal portion 32 and two protruding portions 34. The basal portion 32 is disposed in the receiving element 20 and has a second limiting aperture 36. The protruding portions 34 penetrate the first limiting apertures 27, respectively, and protrude from the receiving element 20. A free end 341 of each protruding portion 34 looks arcuate on a plane in the radial direction.

The resilient element 40 has a first peripheral wall 42 which extends in a circle to take on a tubular shape and a second peripheral wall 44 which extends in a circle to take on a tubular shape. The first peripheral wall 42 has one end defined as a closed end 421 and the other end extended radially and outward to form a connection portion 48 to connect with the second peripheral wall 44. The second peripheral wall 44 has a free end 441 which abuts against the second end wall 23. The first peripheral wall 42 and the second peripheral wall 44 together define annularly a cavity 49. The cavity 49 is in communication with the second tube 26. The first peripheral wall 42 has two through holes 46. The first peripheral wall 42 penetrates the second limiting aperture 36 and is disposed in the first tube 24. The connection portion 48 abuts against the basal portion 32. When the closed end 421 closes the mouth 25, the resilient element 40 is in a closed state as shown in FIG. 5. When the closed end 421 exits the mouth 25, the resilient element 40 is in an open state as shown in FIG. 6. The resilient element 40 switches between the closed state and the open state under an external force, allowing the closed end 421 to movably close the mouth 25.

The operation of the medical connector 10 is described below. Referring to FIG. 5, when infusion is not anticipated, the resilient element 40 is in the closed state. Referring to FIG. 6, when infusion is anticipated, a user connects the first tube 24 to another connector and thus triggers the following events: the free ends 341 of the protruding portions 34 are axially moved, causing the moving element 30 to move from the first end wall 21 to the second end wall 23; the basal portion 32 of the moving element 30 pushes the connection portion 48 to press against the second peripheral wall 44, causing the closed end 421 to exit the mouth 25 so that the resilient element 40 is in the open state; meanwhile, the mouth 25, the through holes 46, the cavity 49, and the second tube 26 are in communication with each other to allow a liquid to enter and exit the cavity 49, thereby effectuating infusion. To terminate the infusion process, the user disconnects the other connector from the first tube 24 so that the moving element 30 is no longer pushed, and the second peripheral wall 44 restores its initial state to allow the closed end 421 to return to the mouth 25 again and close it, thereby effectuating leak prevention.

When the medical connector 10 of the present invention is disconnected, the closed end 421 closes the mouth 25 to prevent leakage. When the medical connector 10 of the present invention is connected, an infusion liquid circulates through the cavity 49 rather than a gap to increase the flow rate of the infusion liquid. Hence, the medical connector 10 of the present invention is suitable for massive liquid infusion. Furthermore, the cavity 49 is filled with a liquid to expel air, thereby preventing air from entering the human body to cause embolism.

The first limiting apertures 27 are penetrated by the protruding portions 34 to ensure that the protruding portions 34 undergo a reciprocating motion only in the axial direction; hence, it is also feasible for the medical connector 10 to have just one first limiting aperture 27 and one protruding portion 34 corresponding in position thereto. The through holes 46 enable the liquid to enter and exit the cavity 49; hence, it is also feasible for the medical connector 10 to have just one through hole 46, though the two through holes 46 enable the liquid to flow more fluently.

Figure 4:
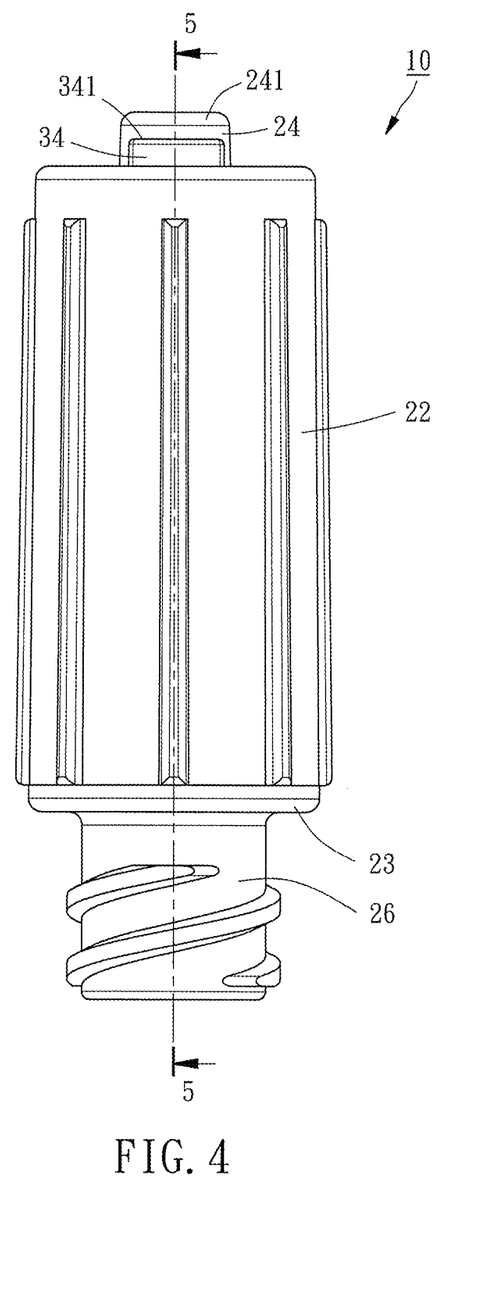
FIG. 4 is a lateral view of the medical connector of the present invention.

To enhance its capability to prevent leakage, the first tube 24 is conical. Referring to FIGS. 4, 5, the inner diameter of the first tube 24 increases gradually from the mouth 25 to the first end wall 21, whereas the outer diameter of the first peripheral wall 42 increases gradually with the inner diameter of the first tube 24. Hence, the outer wall surface of the first peripheral wall 42 is enclosed by the inner wall surface of the first tube 24 as soon as the closed end 421 closes the mouth 25, allowing the through holes 46 to be closed by the inner wall surface of the first tube 24. In another embodiment, the first tube 24 closes the through holes 46 by another means, for example, the first tube 24 has a stop block which protrudes inward and corresponds in position to the through holes 46.

The inner diameter of the second peripheral wall 44 is larger than the inner diameter of the first peripheral wall 42 to maximize the cavity 49 and thus maximize the flow rate, thereby effectuating quick infusion.

The vertical distance between each protruding portion 34 and the first end wall 21 is less than the vertical distance between the free end 241 of the first tube 24 and the first end wall 21 so that the medical connector 10 becomes in communication with another connector step by step, for example, allowing the free end 241 of the first tube 24 to push open the valve of the other connector so that the tubular wall of the other connector pushes and presses against the protruding portions 34.

The basal portion 32 further has a first flange 321 which protrudes toward the second end wall 23. The first flange 321 fits around the second peripheral wall 44 to increase the contact between the basal portion 32 and the connection portion 48, allowing the moving element 30 to push the second peripheral wall 44 efficiently.

The second end wall 23 further has two second flanges 231 which protrude toward the first end wall 21. The free end 441 of the second peripheral wall 44 is clamped between the two second flanges 231. Hence, pushing the second peripheral wall 44 can place a limit on its radial motion, thereby stabilizing the resilient element 40.

The positions of the through holes 46 in this embodiment ensure that a liquid flows fluently through the cavity 49, but the present invention is not limited thereto.

Figure 7:
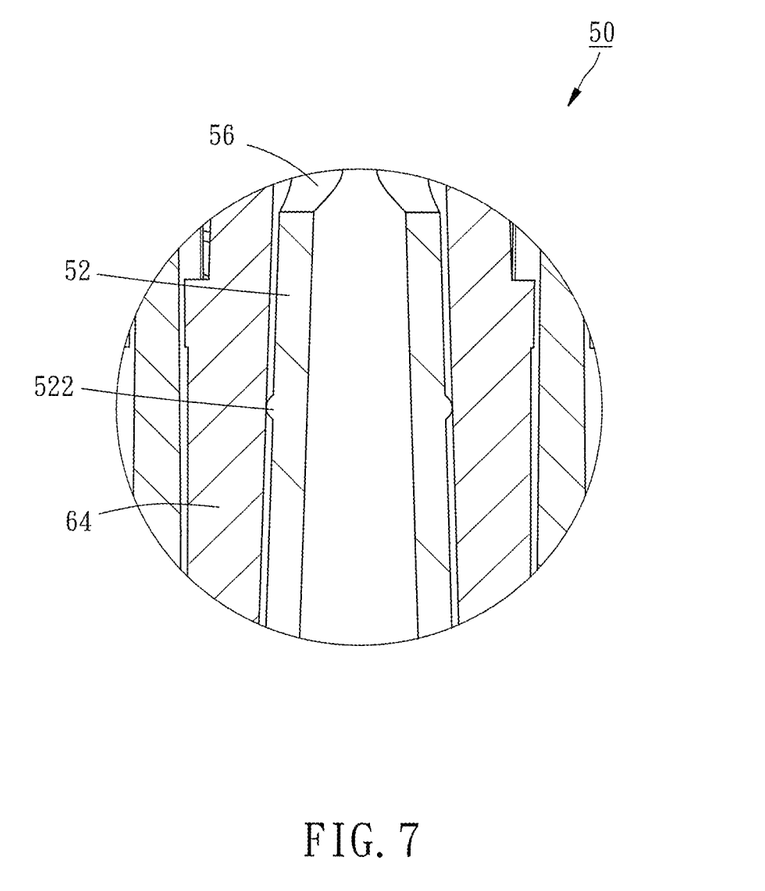
FIG. 7 is a partial enlarged view of another medical connector according to another preferred embodiment of the present invention.

Referring to FIG. 7, a medical connector 50 is provided according to another preferred embodiment of the present invention. A third flange 522 is annularly disposed on the outer wall surface of a first peripheral wall 52 and adapted to better prevent leakage when the medical connector 50 is in the open state. The third flange 522 is disposed between a through hole 56 and a connection portion (not shown). The third flange 522 protrudes toward a first tube 64. When the medical connector 50 is in the open state, the third flange 522 abuts against the inner wall surface of the first tube 64 and thereby hermetically seals any gap which might be present between the first tube 64 and the first peripheral wall 52.

Figure 8:
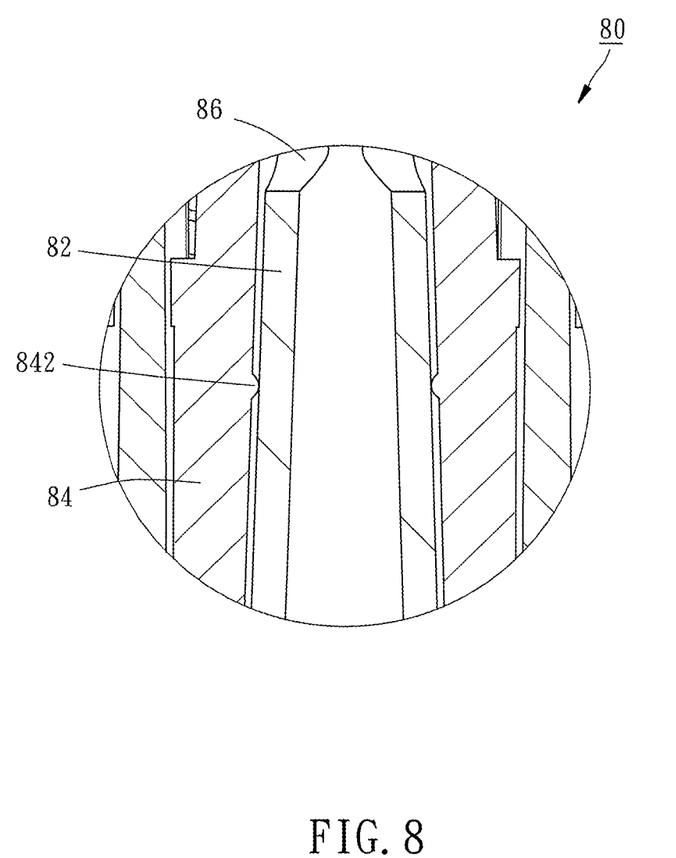
FIG. 8 is a partial enlarged view of yet another medical connector according to yet another preferred embodiment of the present invention.

Referring to FIG. 8, a medical connector 80 is provided according to another preferred embodiment of the present invention. A fourth flange 842 is disposed on the inner wall surface of a first tube 84 and adapted to better prevent leakage when the medical connector 80 is in the open state. The fourth flange 842 protrudes toward a first peripheral wall 82. When the medical connector 80 is in the open state, the fourth flange 842 is abuttingly disposed between a through hole 86 and a connection portion (not shown) to hermetically seal any gap which might be present between the first tube 84 and the first peripheral wall 82.

Although the present invention is disclosed above by embodiments with reference to drawings, the embodiments are illustrative rather than restrictive of technical features and solutions of the present invention. Technical features and solutions which arise from simple modification, replacements, and simplification performed on the embodiments without departing from the spirit of the present invention by persons skilled in the art after studying the technical features and solutions of the present invention shall be deemed falling into the scope of the appended claims.

What is claimed is:

1. A medical connector, comprising:
    a receiving element having an enclosing wall, a first tube, and a second tube, the enclosing wall having a portion extending radially and inward to form a first end wall to connect with the first tube, the enclosing wall having an end extending radially and inward to form a second end wall to connect with the second tube, the first tube having an end which protrudes from the first end wall and has a mouth, wherein an inner diameter of the first tube is least at the mouth, and the first end wall has at least one first limiting aperture, and the second end wall has two second flanges protruding toward the first end wall;
    a moving element having a basal portion and at least one protruding portion connected to the basal portion, the basal portion being disposed in the receiving element and having a second limiting aperture, the protruding portion penetrating the first limiting aperture and protruding from the receiving element; and
    a resilient element having a first peripheral wall extending in a circle to take on a tubular shape and a second peripheral wall extending in a circle to take on a tubular shape, the first peripheral wall having at least one through hole, the first peripheral wall having an end being a closed end, the first peripheral wall having another end extending radially and outward to form a connection portion to connect with the second peripheral wall, the second peripheral wall having a free end abutting against the second end wall, and the free end is clamped between the two second flanges, wherein the first peripheral wall and the second peripheral wall together define annularly a cavity in communication with the second tube, the first peripheral wall penetrating the second limiting aperture and being disposed in the first tube, the closed end movably closing the mouth, the connection portion abutting against the basal portion,
    wherein the moving element moves from the first end wall to the second end wall and thereby presses against the second peripheral wall, causing the closed end to exit the mouth so that the resilient element is in an open state during which the mouth, the through hole, the cavity, and the second tube are in communication with each other.

2. The medical connector of claim 1, wherein the inner diameter of the first tube increases gradually from the mouth to the first end wall, and an outer diameter of the first peripheral wall increases gradually with the inner diameter of the first tube.

3. The medical connector of claim 1, wherein the first tube closes the through hole when the closed end closes the mouth.

4. The medical connector of claim 1, wherein an inner diameter of the second peripheral wall is larger than an inner diameter of the first peripheral wall.

5. The medical connector of claim 1, wherein a vertical distance between the protruding portion and the first end wall is less than a vertical distance between a free end of the first tube and the first end wall.

6. The medical connector of claim 1, wherein the basal portion further has a first flange protruding toward the second end wall and fitting around the second peripheral wall.

* * * * *